(12) United States Patent
Rabolli

(10) Patent No.: US 11,925,783 B2
(45) Date of Patent: *Mar. 12, 2024

(54) PRIMING SYSTEM FOR DRUG DELIVERY DEVICE

(71) Applicant: Becton, Dickinson and Company, Franklin Lakes, NJ (US)

(72) Inventor: Christina Rabolli, Mahwah, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 220 days.

This patent is subject to a terminal disclaimer.

(21) Appl. No.: 17/496,708

(22) Filed: Oct. 7, 2021

(65) Prior Publication Data

US 2022/0023530 A1     Jan. 27, 2022

Related U.S. Application Data

(63) Continuation of application No. 16/238,055, filed on Jan. 2, 2019, now Pat. No. 11,241,527.

(60) Provisional application No. 62/612,842, filed on Jan. 2, 2018.

(51) Int. Cl.
| | |
|---|---|
| *A61M 5/14* | (2006.01) |
| *A61M 5/142* | (2006.01) |
| *G06F 3/0482* | (2013.01) |
| *G16H 80/00* | (2018.01) |
| *H04L 67/55* | (2022.01) |

(52) U.S. Cl.
CPC .............. *A61M 5/14* (2013.01); *G16H 80/00* (2018.01); *H04L 67/55* (2022.05); *A61M 2005/1402* (2013.01); *A61M 2005/14252* (2013.01); *G06F 3/0482* (2013.01)

(58) Field of Classification Search
CPC ............ A61M 5/14; A61M 2005/1402; A61M 2005/14252; A61M 5/14248; A61M 5/001; A61M 5/14244; A61M 5/158; A61M 2205/582; A61M 2205/583
See application file for complete search history.

(56) References Cited

U.S. PATENT DOCUMENTS

| | | | | |
|---|---|---|---|---|
| 5,232,454 A | * | 8/1993 | Hollister | ............. A61M 5/3216 604/110 |
| 9,833,573 B2 | | 12/2017 | Edwards et al. | |
| 10,806,855 B2 | | 10/2020 | Destefano et al. | |

(Continued)

FOREIGN PATENT DOCUMENTS

| | | |
|---|---|---|
| CA | 2962643 A1 | 4/2016 |
| CN | 1960776 A | 5/2007 |

(Continued)

*Primary Examiner* — James D Ponton
(74) *Attorney, Agent, or Firm* — The Webb Law Firm

(57) ABSTRACT

A priming assembly for a drug delivery device includes a hub, a base connected to the hub and moveable relative to the hub between a first position and a second position, with the base defining a passageway, a cap defining an interior chamber and a passageway in fluid communication with the interior chamber, and a needle connected to the hub and positioned within the interior chamber of the cap, where the passageway of the base is in fluid communication with the passageway of the cap when the base is in the first position, and where the passageway of the base is isolated from the passageway of the cap when the base is in the second position.

19 Claims, 17 Drawing Sheets

(56) References Cited

U.S. PATENT DOCUMENTS

| | | |
|---|---|---|
| 2004/0254543 A1 | 12/2004 | Griffiths |
| 2007/0224055 A1* | 9/2007 | Anex ..................... F04B 19/04 |
| | | 417/404 |
| 2009/0171324 A1 | 7/2009 | Chong et al. |
| 2010/0137808 A1 | 6/2010 | Wilmot et al. |
| 2011/0172601 A1 | 7/2011 | Beebe et al. |
| 2012/0220949 A1* | 8/2012 | Davies ................... A61M 5/34 |
| | | 604/93.01 |
| 2013/0006107 A1 | 1/2013 | Koyama |
| 2013/0237932 A1 | 9/2013 | Thueer et al. |
| 2013/0274702 A1 | 10/2013 | Miyasaka |
| 2014/0081239 A1 | 3/2014 | Cronenberg |
| 2017/0335478 A1 | 11/2017 | Chen et al. |

FOREIGN PATENT DOCUMENTS

| | | |
|---|---|---|
| CN | 102271735 A | 12/2011 |
| EP | 2457602 A1 | 11/2010 |
| GB | 2480407 A | 11/2011 |
| JP | 2011245050 A | 12/2011 |
| JP | 2015195849 A | 11/2015 |
| WO | 2006057636 A1 | 6/2006 |
| WO | 2011118410 A1 | 9/2011 |
| WO | 2011150184 A2 | 12/2011 |
| WO | 2014144416 A1 | 9/2014 |
| WO | 2016053954 A1 | 4/2016 |

* cited by examiner

PRIMING SYSTEM FOR DRUG DELIVERY DEVICE

CROSS-REFERENCE TO RELATED APPLICATION

The present application is a continuation of U.S. patent application Ser. No. 16/238,055 entitled "Priming System for Drug Delivery Device" filed Jan. 2, 2019, which claims priority to U.S. Provisional Application Ser. No. 62/612,842 entitled "Priming System for Drug Delivery Device" filed Jan. 2, 2018, the entire disclosure of each of which are hereby incorporated by reference.

BACKGROUND OF THE INVENTION

Field of the Invention

The present disclosure relates generally to a drug delivery device and, in particular, to a priming assembly for a drug delivery device.

Description of Related Art

Various types of automatic injection or drug delivery devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. When the volume of fluid or drug to be administered is generally below a certain volume, such as 1 mL, an auto-injector is typically used, which typically has an injection time of about 10 to 15 seconds. When the volume of fluid or drug to be administered is above 1 mL, the injection time generally becomes longer resulting in difficulties for the patient to maintain contact between the device and the target area of the patient's skin. Further, as the volume of drug to be administered becomes larger, increasing the time period for injection becomes desirable. The traditional method for a drug to be injected slowly into a patient is to initiate an IV and inject the drug into the patient's body slowly. Such a procedure is typically performed in a hospital or outpatient setting.

Certain devices allow for self-injection in a home setting and are capable of gradually injecting a liquid therapeutic preparation into the skin of a patient. In some cases, these devices are small enough (both in height and in overall size) to allow them to be "worn" by a patient while the liquid therapeutic preparation is being infused into the patient. These devices typically include a pump or other type of discharge mechanism to force the liquid therapeutic preparation to flow out of a reservoir and into the injection needle. Such devices also typically include a valve or flow control mechanism to cause the liquid therapeutic preparation to begin to flow at the proper time and a triggering mechanism to initiate the injection.

SUMMARY OF THE INVENTION

In one aspect, a priming assembly for a drug delivery device includes a hub, a base connected to the hub and moveable relative to the hub between a first position and a second position, with the base defining a passageway, a cap defining an interior chamber and a passageway in fluid communication with the interior chamber, and a needle connected to the hub and positioned within the interior chamber of the cap. The passageway of the base is in fluid communication with the passageway of the cap when the base is in the first position, and the passageway of the base is isolated from the passageway of the cap when the base is in the second position.

The cap and the base may form a sealed interface between the cap and the base. The cap may include a closed first end and an open second end, with the open second end secured to the hub. The cap may be manufactured from an elastomeric material. The cap is configured to deform from a first position where an end of the needle is positioned within the cap and a second position where the end of the needle is positioned outside of the cap. One of the hub and the base may define a slot and the other of the hub and the base may include a projection received within the slot, with the slot having a first end and a second end, and where, when the projection is at the first end of the slot, the base is in the first position, and, when the projection is at the second end of the slot, the base is in the second position. The assembly may further include a priming fluid tube in fluid communication with the passageway of the base. The assembly may further include a delivery tube connected to the hub and in fluid communication with the needle.

In a further aspect, a drug delivery device includes a housing, a cartridge received within the housing with the cartridge configured to receive a medicament, a drive assembly received with the housing and configured to engage the cartridge and dispense medicament from the cartridge, a needle actuator assembly received within the housing with the needle actuator assembly including a patient needle configured to pierce a user's skin, and a priming system. The priming system includes a cartridge priming assembly including a hub, a base connected to the hub and moveable relative to the hub between a first position and a second position, a cap defining an interior chamber and a passageway in fluid communication with the interior chamber, and a needle connected to the hub and positioned within the interior chamber of the cap. The base defines a passageway. The priming system further includes a needle actuator priming assembly including a hub, a base connected to the hub and moveable relative to the hub between a first position and a second position, a cap defining an interior chamber and a passageway in fluid communication with the interior chamber, and a needle connected to the hub and positioned within the interior chamber of the cap, with the base defining a passageway. The priming system also includes a delivery tube in fluid communication with the hub of the cartridge priming assembly and the hub of the needle actuator priming assembly. The passageway of the base of the cartridge priming assembly is in fluid communication with the passageway of the cap of the cartridge priming assembly when the base is in the first position, and the passageway of the base of the cartridge priming assembly is isolated from the passageway of the cap when the base is in the second position.

The passageway of the base of the needle actuator priming assembly may be in fluid communication with the passageway of the cap of the needle actuator priming assembly when the base is in the first position, and the passageway of the base cartridge of the needle actuator priming assembly may be isolated from the passageway of the cap when the base is in the second position. The device may further include an inflow tube in fluid communication with the passageway of the base of the cartridge priming assembly. The device may further include an outflow tube in fluid communication with the passageway of the base of the needle actuator priming assembly. The cap and the base of the cartridge priming assembly and the needle actuator priming assembly may each form a sealed interface between the cap and the base. The caps of the cartridge priming assembly and the needle actuator priming assembly may each include a closed first end and an open second end, with the open second ends secured to the respective hubs. The caps of the cartridge priming assembly and the needle actuator priming assembly may each comprise an elastomeric material. The caps of the cartridge priming assembly and the needle actuator priming assembly may each be configured to deform from a first position where an end of the needle is positioned within the cap and a second position where the end of the needle is positioned outside of the cap. One of the hub and the base of the cartridge priming assembly may define a slot and the other of the hub and the base may include a projection received within the slot, with the slot having a first end and a second end, and where, when the projection is at the first end of the slot, the base is in the first position, and, when the projection is at the second end of the slot, the base is in the second position.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

DETAILED DESCRIPTION

Figure 1:
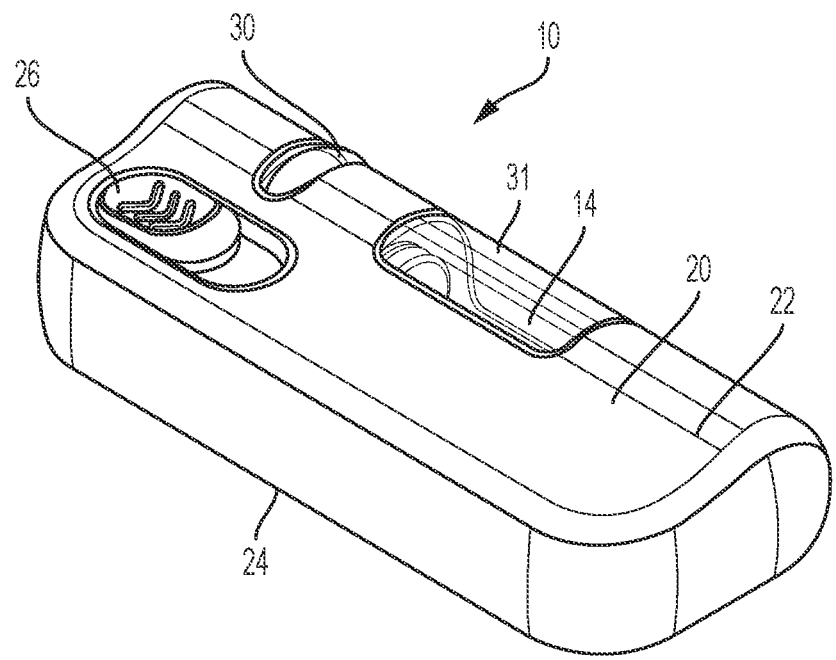
FIG. 1 is a perspective view of a drug delivery system according to one aspect of the present invention.
Figure 2:
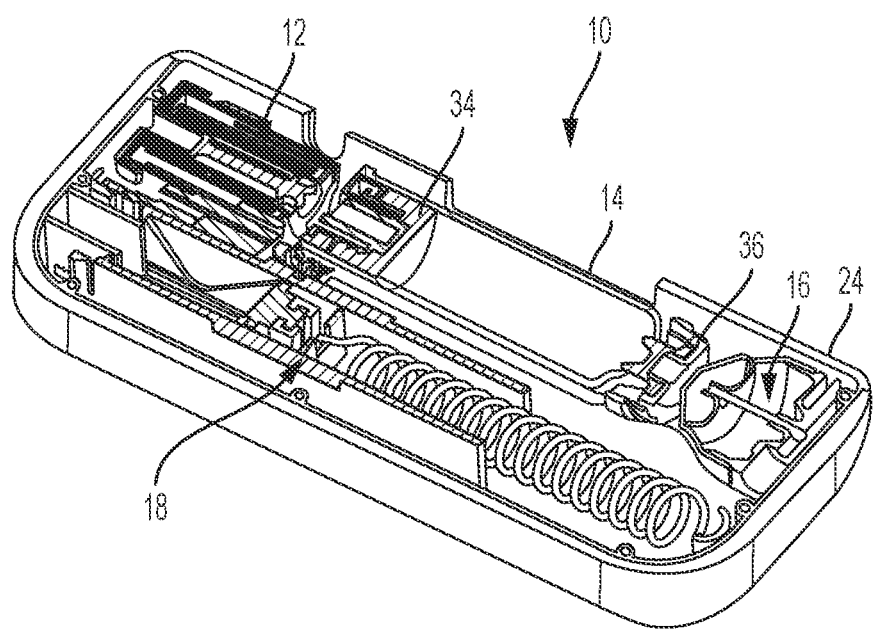
FIG. 2 is a perspective, cross-sectional view of the drug delivery system of FIG. 1 according to one aspect of the present invention.
Figure 3:
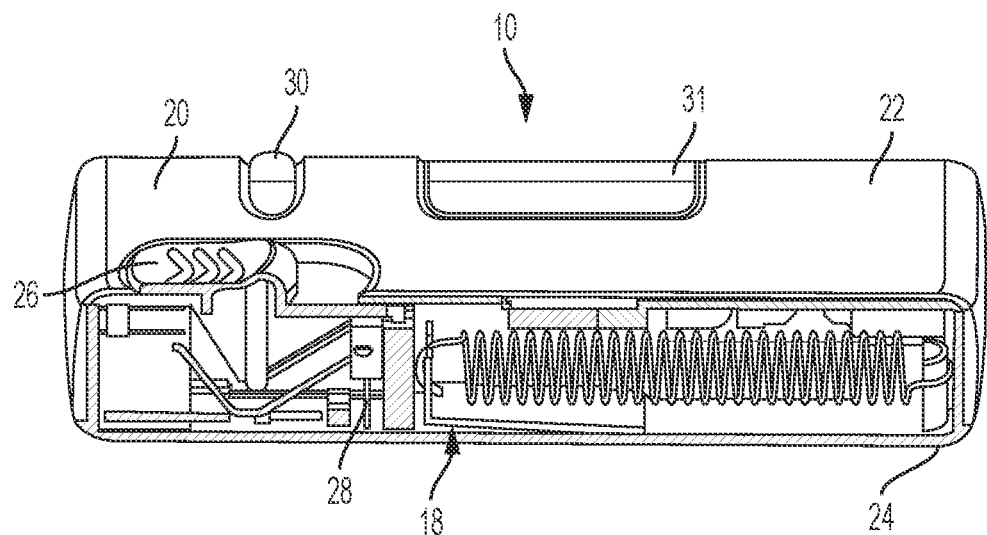
FIG. 3 is a front, cross-sectional view of the drug delivery system of FIG. 1 according to one aspect of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-15, a drug delivery device 10 according to one aspect of the present disclosure includes a drive assembly 12, a container 14, a valve assembly 16, and a needle actuator assembly 18. The drive assembly 12, the container 14, the valve assembly 16, and the needle actuator assembly 18 are at least partially positioned within a cavity defined by a housing 20. The housing 20 includes a top portion 22 and a bottom portion 24, although other suitable arrangements for the housing 20 may be utilized. In one aspect, the drug delivery device 10 is an injector device configured to be worn or secured to a user and to deliver a predetermined dose of a medicament provided within the container 14 via injection into the user. The device 10 may be utilized to deliver a "bolus injection" where a medicament is delivered within a set time period. The medicament may be delivered over a time period of up to 45 minutes, although other suitable injection amounts and durations may be utilized. A bolus administration or delivery can be carried out with rate controlling or have no specific rate controlling. The device 10 may deliver the medicament at a fixed pressure to the user with the rate being variable. The general operation of the device 10 is described below in reference to FIGS. 1-15.

Referring again to FIGS. 1-15, the device 10 is configured to operate through the engagement of an actuation button 26 by a user, which results in a needle 28 of the needle actuator assembly 18 piercing the skin of a user, the actuation of the drive assembly 12 to place the needle 28 in fluid communication with the container 14 and to expel fluid or medicament from the container 14, and the withdrawal of the needle 28 after injection of the medicament is complete. The general operation of a drug delivery system is shown and described in International Publication Nos. 2013/155153 and 2014/179774, which are hereby incorporated by reference in their entirety. The housing 20 of the device 10 includes an indicator window 30 for viewing an indicator arrangement 32 configured to provide an indication to a user on the status of the device 10 and a container window 31 for viewing the container 14. The indicator window 30 may be a magnifying lens for providing a clear view of the indicator arrangement 32. The indicator arrangement 32 moves along with the needle actuator assembly 18 during use of the device 10 to indicate a pre-use status, use status, and post-use status of the device 10. The indicator arrangement 32 provides visual indicia regarding the status, although other suitable indicia, such an auditory or tactile, may be provided as an alternative or additional indicia.

Figure 4:
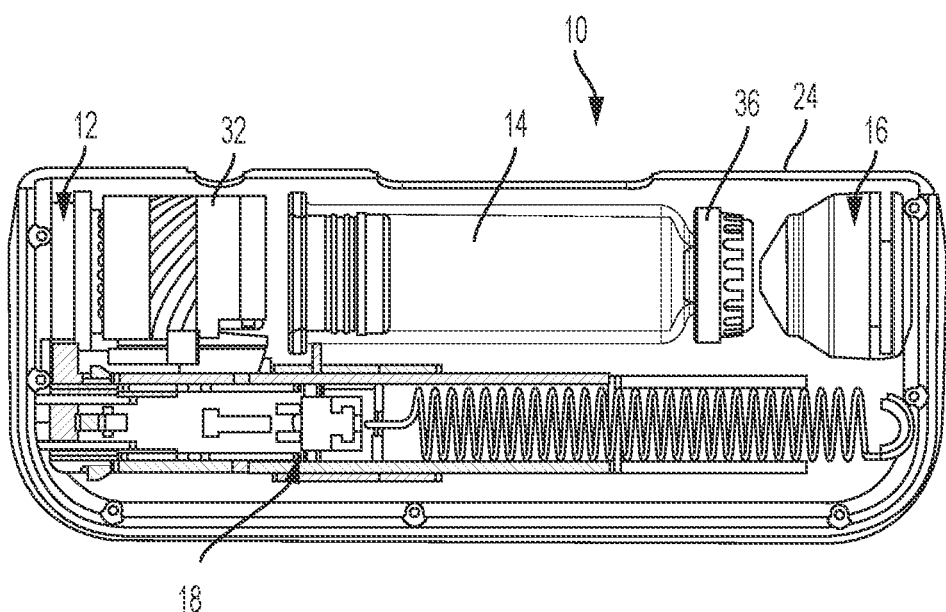
FIG. 4 is a top view of the drug delivery system of FIG. 1 according to one aspect of the present invention, showing a top portion of the housing removed and the drug delivery system in a pre-use position.
Figure 5:
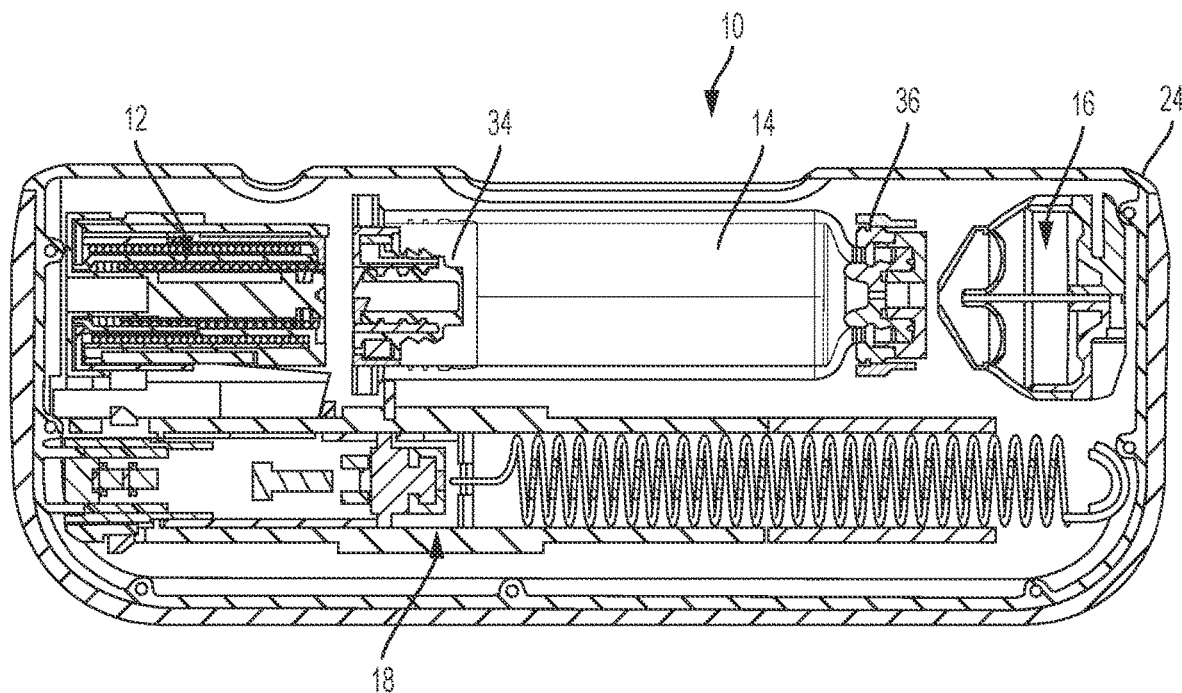
FIG. 5 is a top, cross-sectional view of the drug delivery system of FIG. 1 according to one aspect of the present invention, showing the drug delivery system in a pre-use position.
Figure 6:
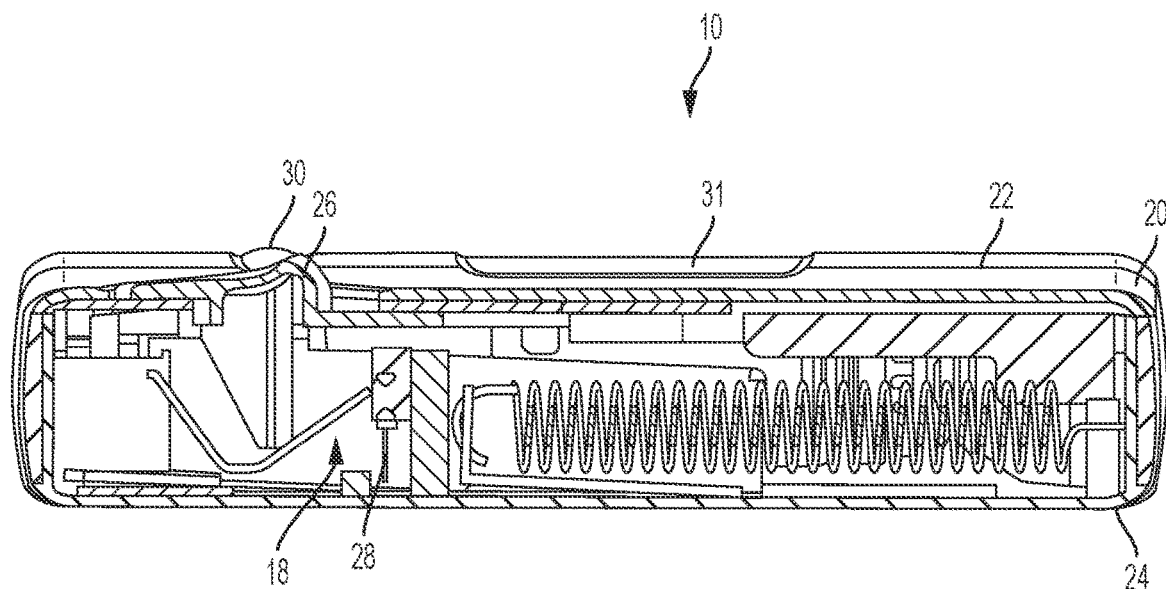
FIG. 6 is a front, cross-sectional view of the drug delivery system of FIG. 1 according to one aspect of the present invention, showing the drug delivery system in a pre-use position.
Figure 7:
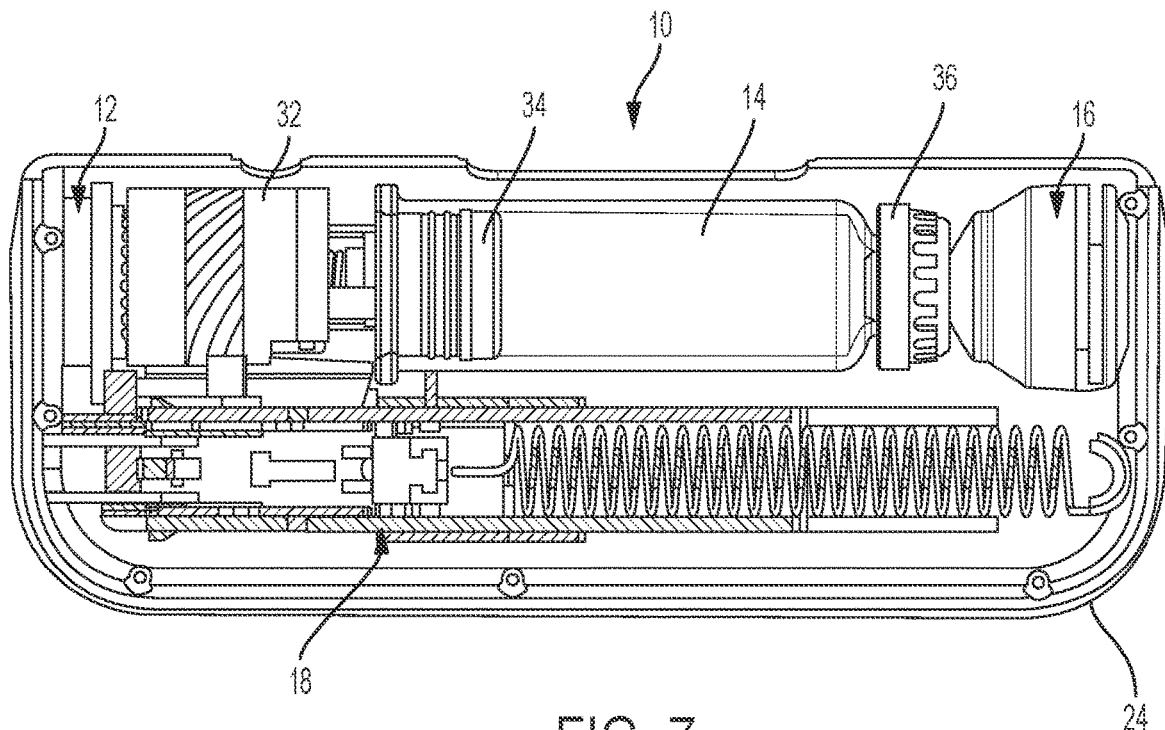
FIG. 7 is a top view of the drug delivery system of FIG. 1 according to one aspect of the present invention, showing a top portion of the housing removed and the drug delivery system in an initial actuation position.
Figure 8:
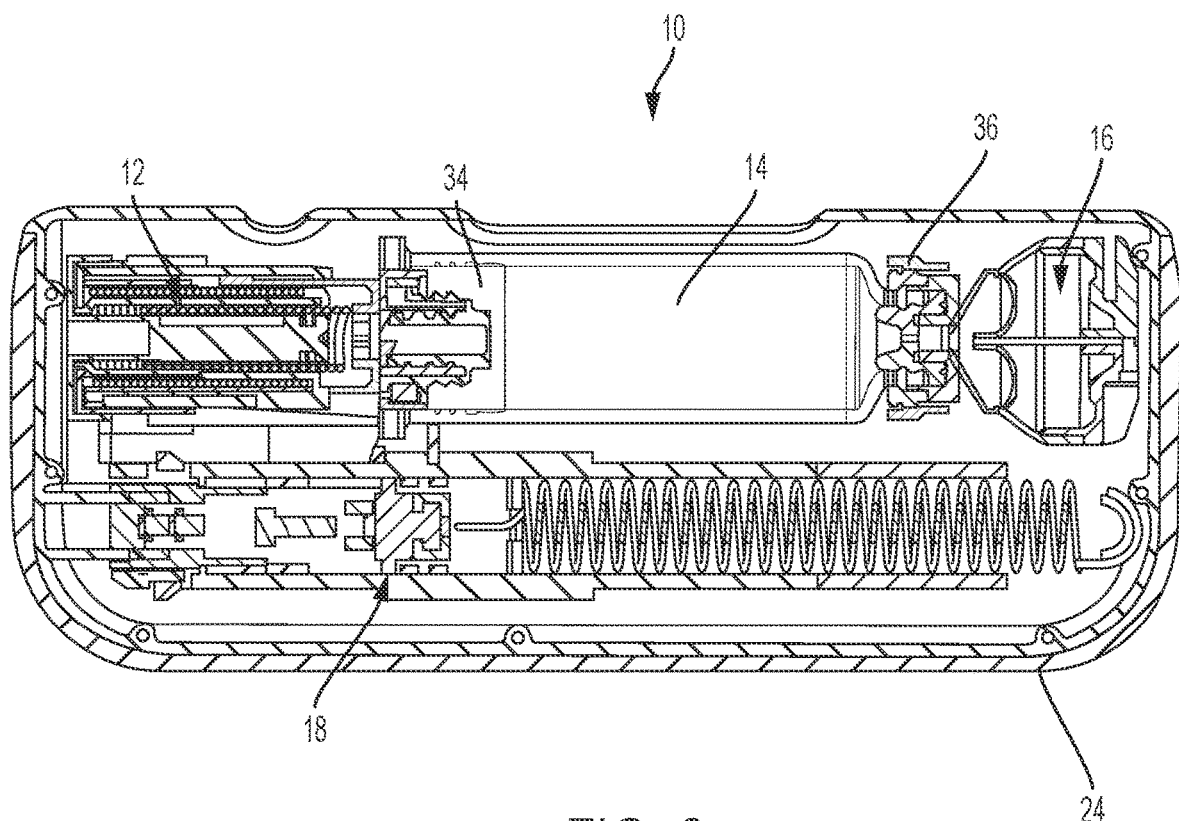
FIG. 8 is a top, cross-sectional view of the drug delivery system of FIG. 1 according to one aspect of the present invention, showing the drug delivery system in an initial actuation position.
Figure 9:
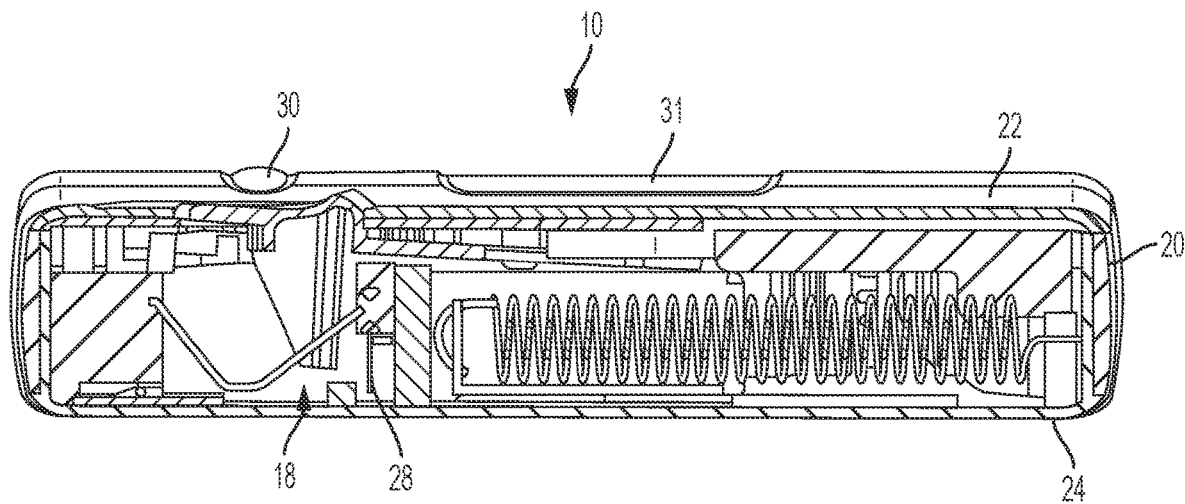
FIG. 9 is a front, cross-sectional view of the drug delivery system of FIG. 1 according to one aspect of the present invention, showing the drug delivery system in an initial actuation position.

Referring to FIGS. 4-6, during a pre-use position of the device 10, the container 14 is spaced from the drive assembly 12 and the valve assembly 16 and the needle 28 is in a retracted position. During the initial actuation of the device 10, as shown in FIGS. 7-9, the drive assembly 12 engages the container 14 to move the container 14 toward the valve assembly 16, which is configured to pierce a closure 36 of the container 14 and place the medicament within the container 14 in fluid communication with the needle 28 via a tube (not shown) or other suitable arrangement. The drive assembly 12 is configured to engage a stopper 34 of the container 14, which will initially move the entire container 14 into engagement with the valve assembly 16 due to the incompressibility of the fluid or medicament within the container 14. The initial actuation of the device 10 is caused by engagement of the actuation button 26 by a user, which releases the needle actuator assembly 18 and the drive assembly 12 as discussed below in more detail. During the initial actuation, the needle 28 is still in the retracted position and about to move to the extended position to inject the user of the device 10.

Figure 10:
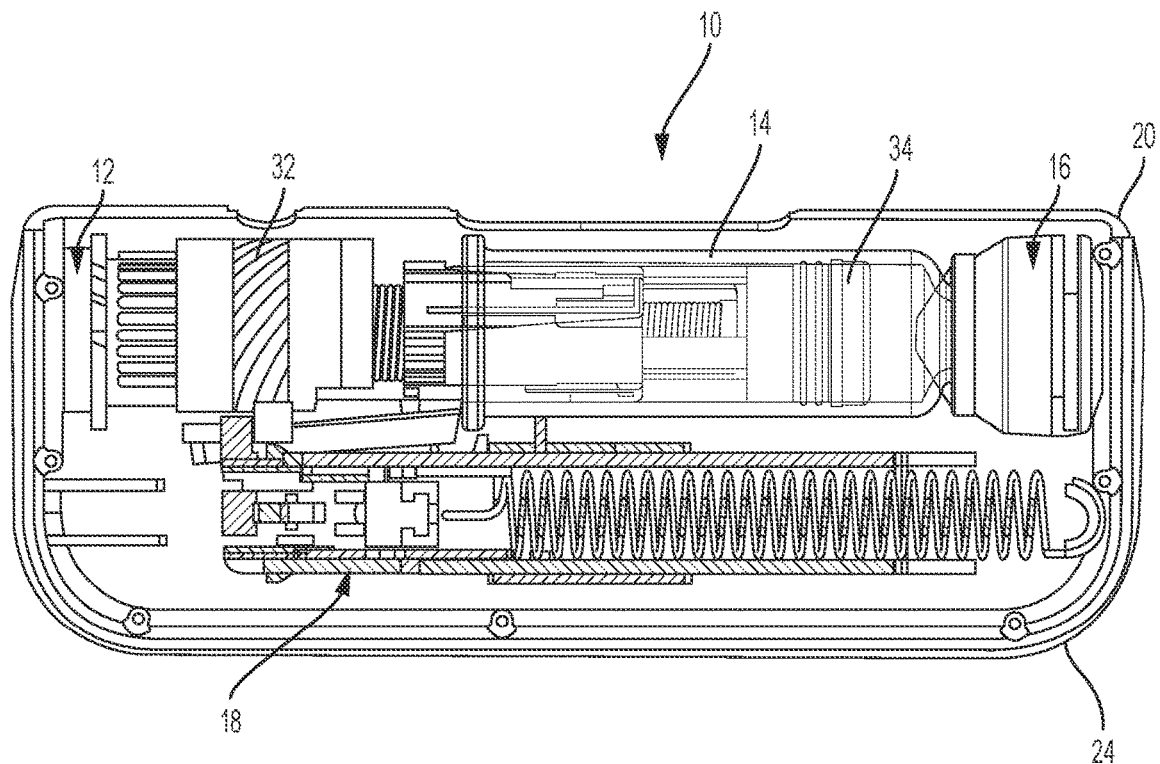
FIG. 10 is a top view of the drug delivery system of FIG. 1 according to one aspect of the present invention, showing a top portion of the housing removed and the drug delivery system in a use position.
Figure 11:
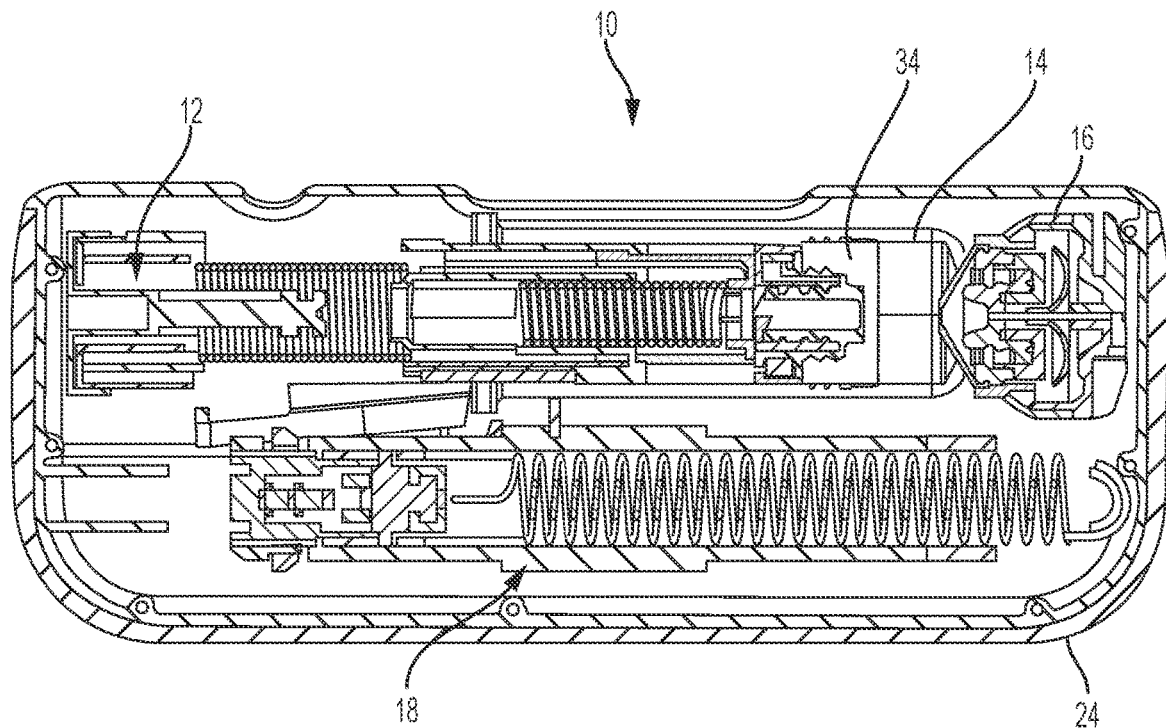
FIG. 11 is a top, cross-sectional view of the drug delivery system of FIG. 1 according to one aspect of the present invention, showing the drug delivery system in a use position.
Figure 12:
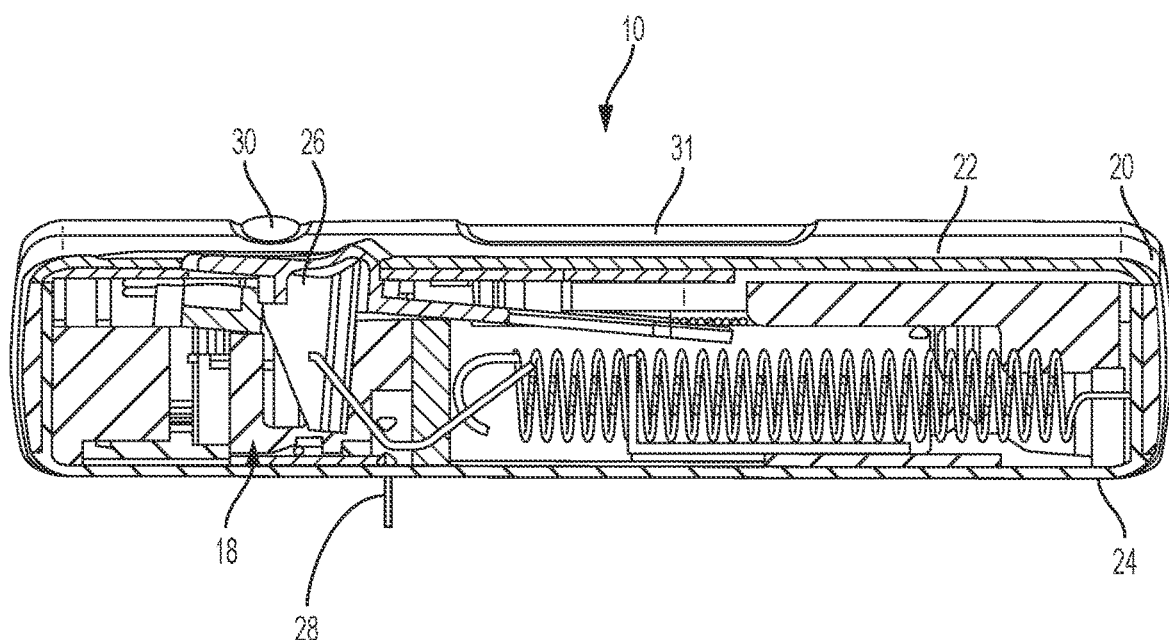
FIG. 12 is a front, cross-sectional view of the drug delivery system of FIG. 1 according to one aspect of the present invention, showing the drug delivery system in a use position.
Figure 13:
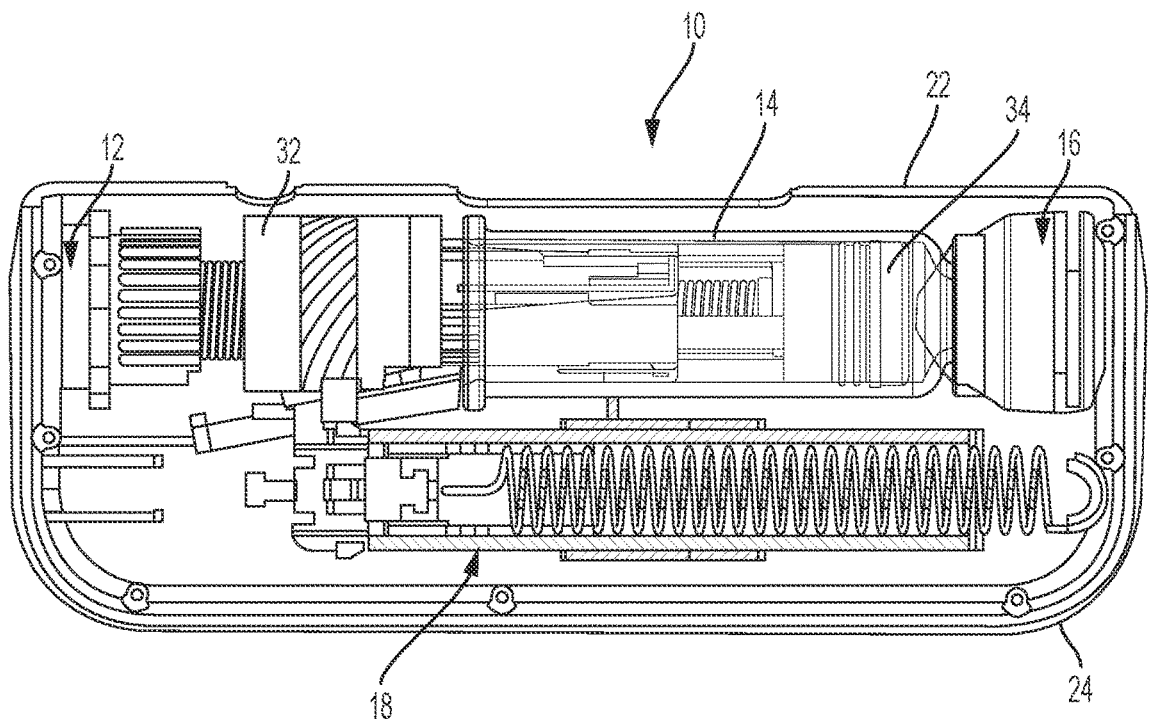
FIG. 13 is a top view of the drug delivery system of FIG. 1 according to one aspect of the present invention, showing a top portion of the housing removed and the drug delivery system in a post-use position.
Figure 14:
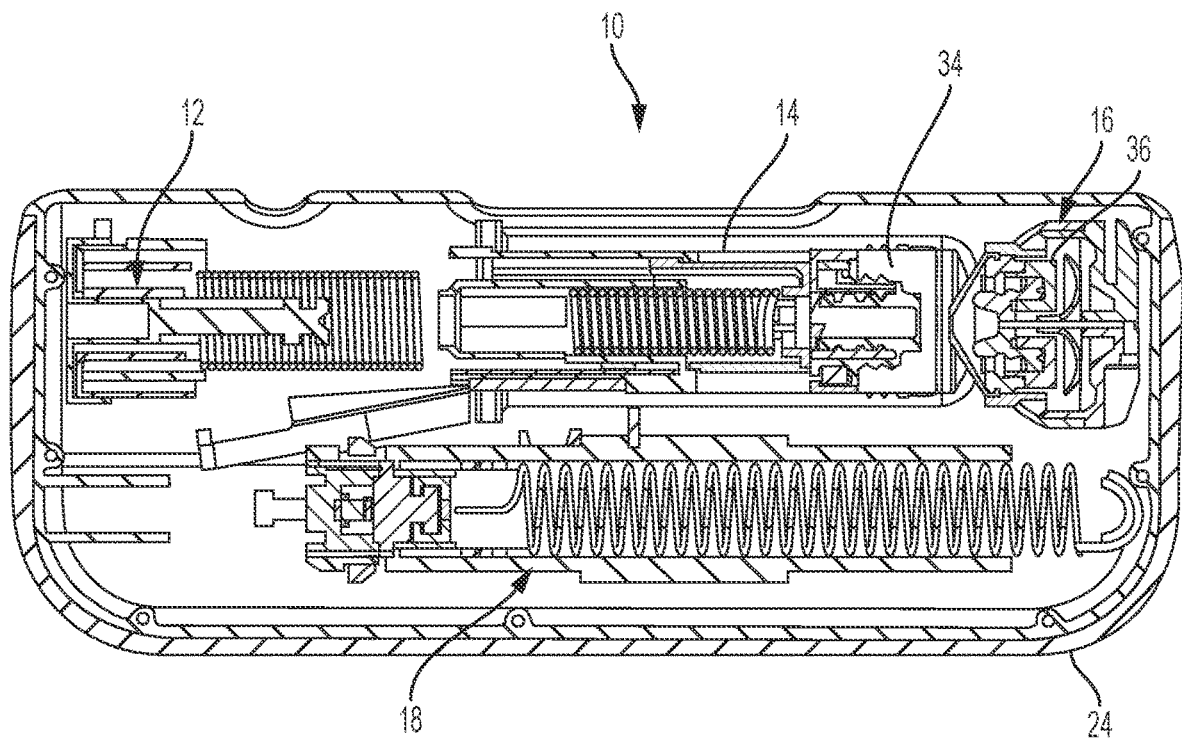
FIG. 14 is a top, cross-sectional view of the drug delivery system of FIG. 1 according to one aspect of the present invention, showing the drug delivery system in a post-use position.
Figure 15:
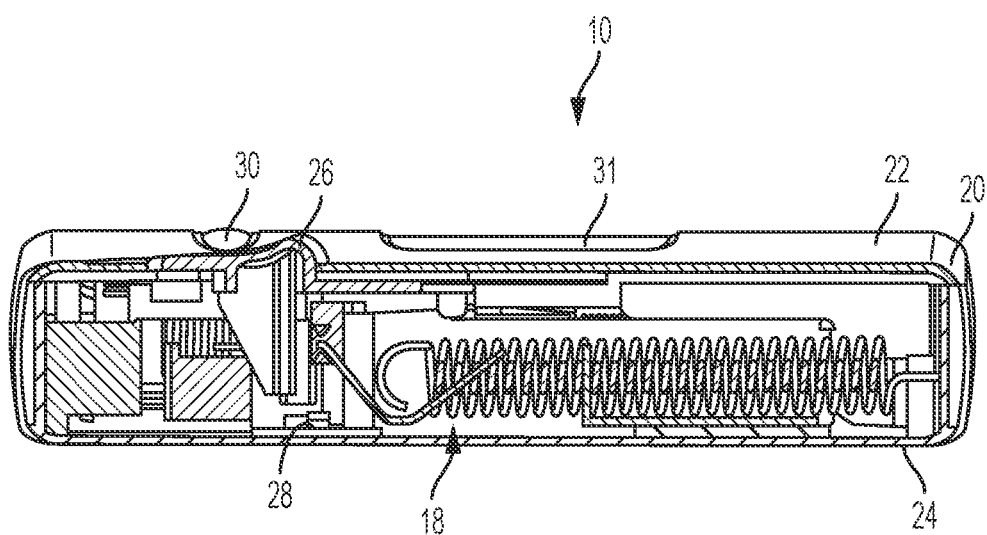
FIG. 15 is a front, cross-sectional view of the drug delivery system of FIG. 1 according to one aspect of the present invention, showing the drug delivery system in a post-use position.
Figure 16:
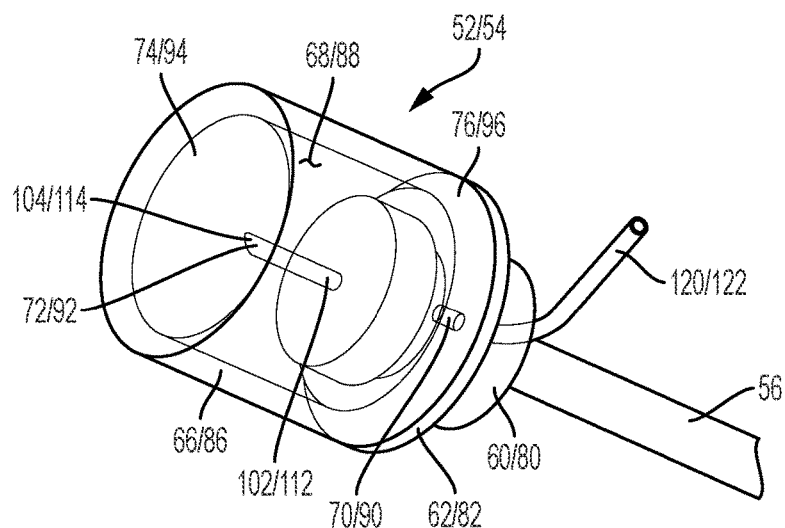
FIG. 16 is a perspective view of a priming assembly according to one aspect of the present invention, showing the assembly in an open position and with a cap shown as transparent for clarity.
Figure 17:
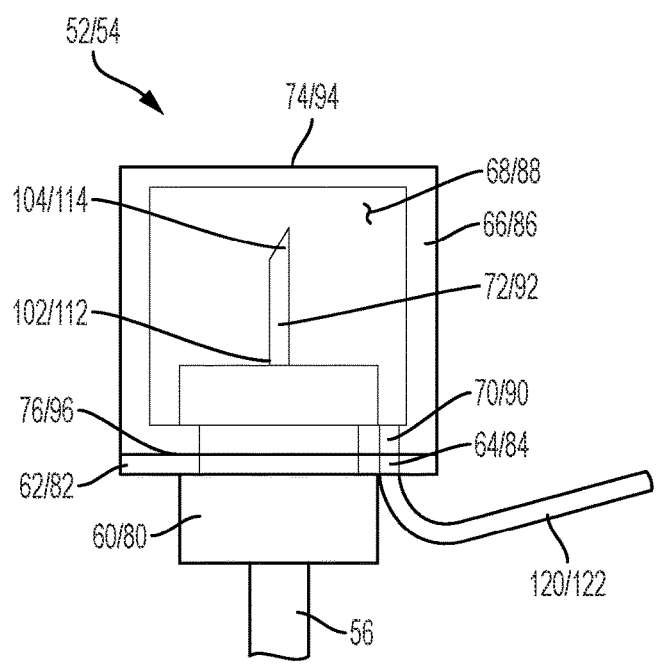
FIG. 17 is a front view of the priming assembly of FIG. 16 according to one aspect of the present invention, showing the assembly in an open position.
Figure 18:
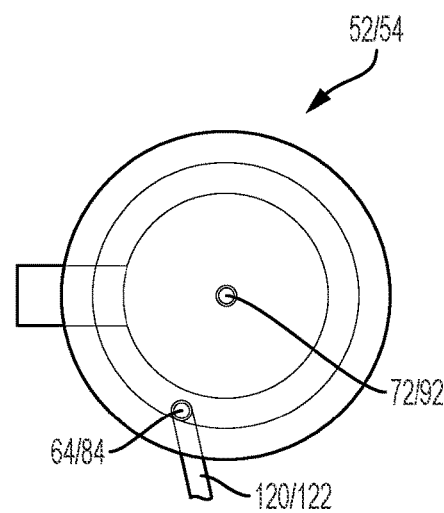
FIG. 18 is a top view of the priming assembly of FIG. 16 according to one aspect of the present invention, showing the assembly in an open position.
Figure 19:
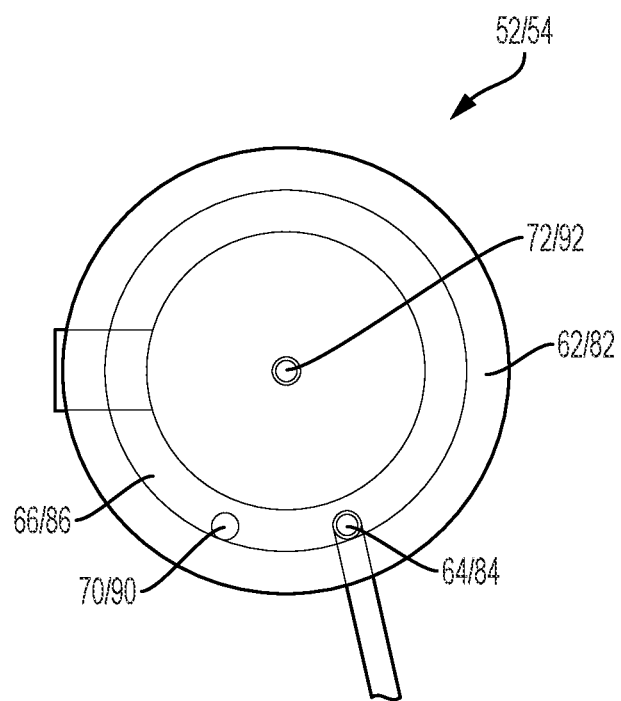
FIG. 19 is a top view of the priming assembly of FIG. 16 according to one aspect of the present invention, showing the assembly in a closed position.
Figure 20:
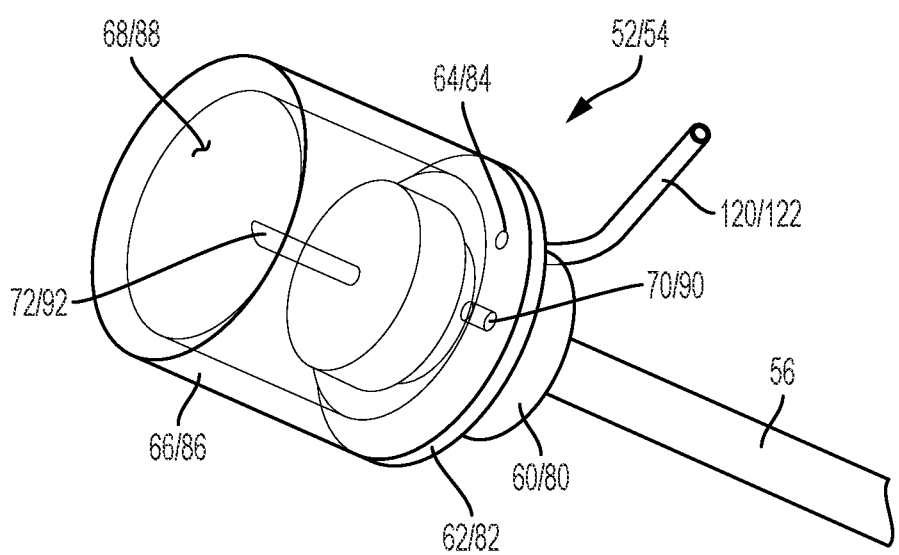
FIG. 20 is a perspective view of the priming assembly of FIG. 16 according to one aspect of the present invention, showing the assembly in a closed position.
Figure 21:
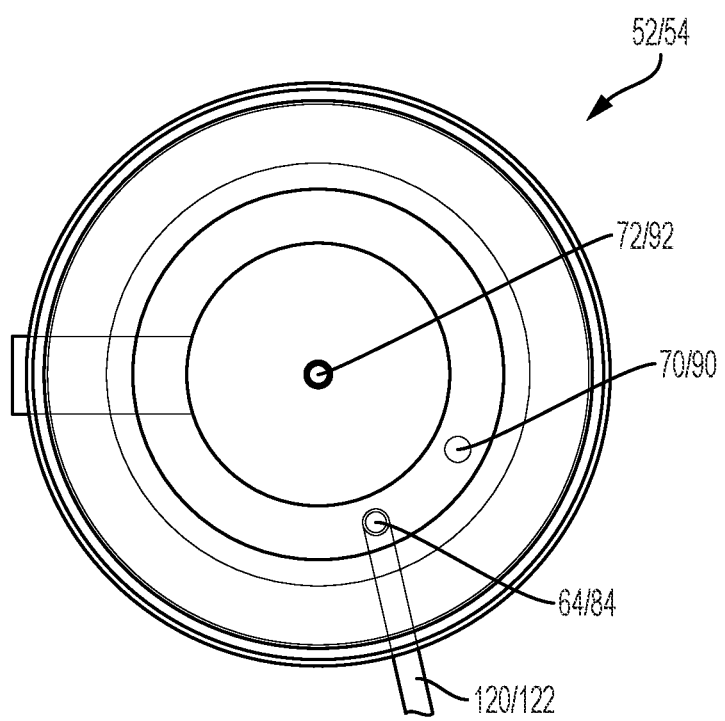
FIG. 21 is a top view of the priming assembly of FIG. 16 according to one aspect of the present invention, showing the assembly in a use position.
Figure 22:
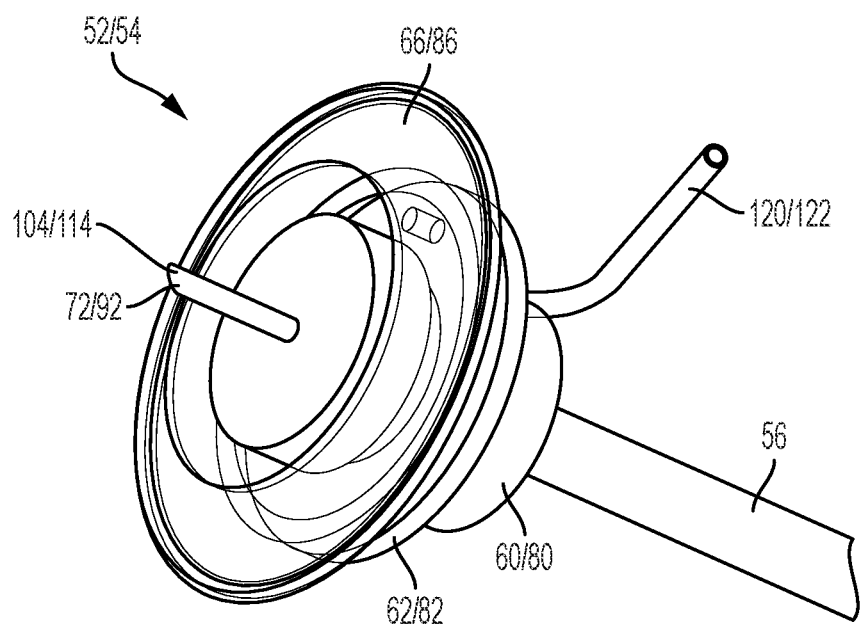
FIG. 22 is a perspective view of the priming assembly of FIG. 16 according to one aspect of the present invention, showing the assembly in a use position.

During the use position of the device 10, as shown in FIGS. 10-12, the needle 28 is in the extended position at least partially outside of the housing 20 with the drive assembly 12 moving the stopper 34 within the container 14 to deliver the medicament from the container 14, through the needle 28, and to the user. In the use position, the valve assembly 16 has already pierced a closure 36 of the container 14 to place the container 14 in fluid communication with the needle 28, which also allows the drive assembly 12 to move the stopper 34 relative to the container 14 since fluid is able to be dispensed from the container 14. At the post-use position of the device 10, shown in FIGS. 13-15, the needle 28 is in the retracted position and engaged with a pad 38 to seal the needle 28 and prevent any residual flow of fluid or medicament from the container 14. The container 14 and valve assembly 16 may be the container 14 and valve assembly 16 shown and described in International Publication No. WO 2015/081337, which is hereby incorporated by reference in its entirety.

Referring to FIGS. 16-25, a priming system 50 for use in connection with the drug delivery device 10 is shown. Although the priming system 50 is shown in connection with the delivery device 10, the priming system 50 may also be incorporated into any other suitable device or system for delivering medicament to patient. The priming system 50 includes a cartridge priming assembly 52, a needle actuator priming assembly 54, and a delivery tube 56 extending between the cartridge priming assembly 52 and the needle actuator priming assembly 54.

Referring to FIGS. 16-22, each of the priming assemblies 52, 54 includes a hub 60, 80, a base 62, 82 connected to the hub 60, 80 and defining a passageway 64, 84, a cap 66, 86 defining an interior chamber 68, 88 and a passageway 70, 90 in fluid communication with the interior chamber 68, 88, and a needle 72, 92 connected to the hub 60, 80 and positioned within the interior chamber 68, 88 of the cap 66, 86. The base 62, 82 is moveable relative to the hub 60, 80 between a first positon and a second position. In particular, the base 62, 82 is rotatable relative to the cap 66, 86 and the hub 60, 80 between the first and second positions. The delivery tube 56 is in fluid communication with the hub 60 of the cartridge priming assembly 52 and the hub 80 of the needle actuator priming assembly 54. For each assembly 52, 54, the passageway 64, 84 of the base 62, 82 is in fluid communication with the passageway 70, 90 of the cap 66, 86 when the base 62, 82 is in the first position, and the passageway 64, 84 of the base 62, 82 is isolated from the passageway 70, 90 of the cap 66, 86 when the base 62, 82 is in the second position. The cap 66, 86 and the base 62, 82 of the priming assemblies 52, 54 each form a sealed interface between the cap 66, 86 and the base 62, 82. The sealed interface prevents any leakage from the passageway 70, 90 of the cap 66, 86 during movement of the base 62, 82 between the first and second positions. The sealed interface may be provided by the engagement between the cap 66, 86 and the base 62, 82. In particular, the cap 66, 86 may be manufactured from an elastomeric material that forms a seal with the base 62, 82 and the hub 60, 80. The cap 66, 86 includes a closed first end 74, 94 and an open second end 76, 96, with the open second end 76, 96 positioned over and secured to the hub 60, 80. The open second end 76, 96 is engaged with the base 62, 82.

Referring again to FIGS. 16-22, the needle 72, 92 includes a first end 102, 112 secured to and in fluid communication with the hub 60, 80 and a second end 104, 114 positioned within the interior chamber 68, 88 of the cap 66, 86. The second end 104, 114 of the needle 72, 92 may be sharpened and configured to pierce the cap 66, 86 and a closure 36 of the cartridge 14. For each of the priming assemblies 52, 54, the cap 66, 86 is configured to deform from a first, pre-use position where the second end 104, 114 of the needle 72, 92 is positioned within the cap 66, 86 and a second, use position where the second end 104, 114 of the needle 72, 92 is positioned outside of the cap 66, 86.

Referring again to FIGS. 16-25, the cartridge priming assembly 52 includes an inflow tube 120 in fluid communication with the passageway 64 of the base 62 of the cartridge priming assembly 52. The needle actuator priming assembly 54 includes an outflow tube 122 in fluid communication with the passageway 84 of the base 82 of the needle actuator priming assembly 54.

Figure 23:
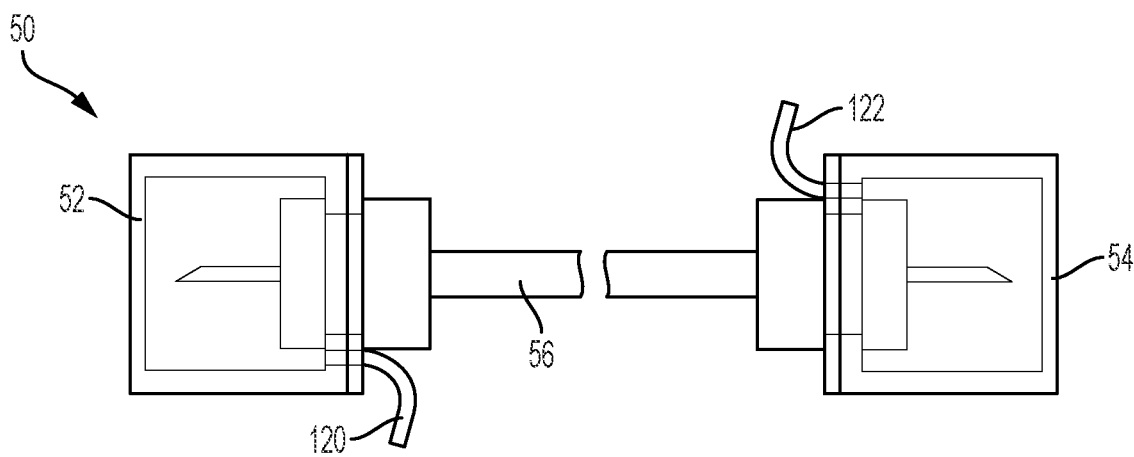
FIG. 23 is a front view of a priming system according to one aspect of the present invention, showing an open position of the system.
Figure 24A:
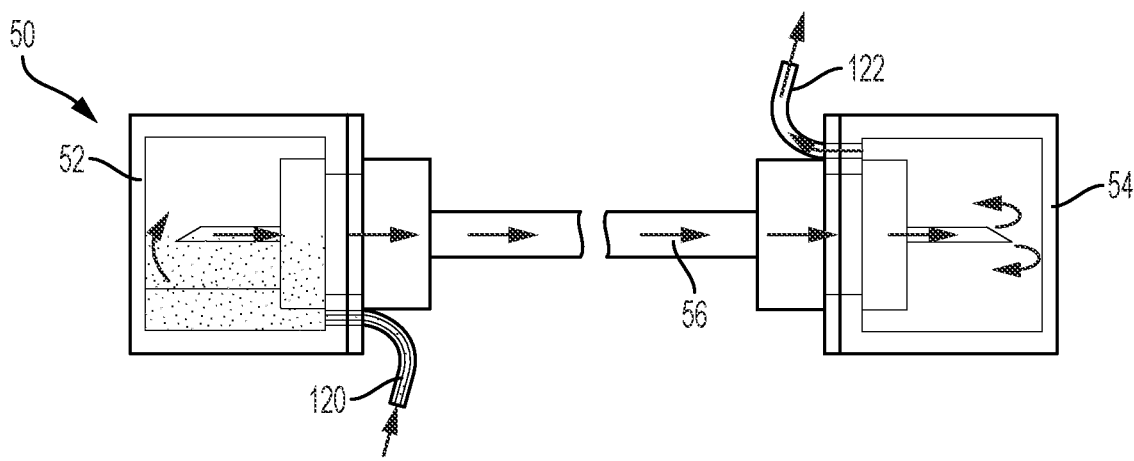
FIG. 24A is a front view of the priming system of FIG. 23 according to one aspect of the present invention, showing an open position of the system while fluid fills the fluid path.
Figure 24B:
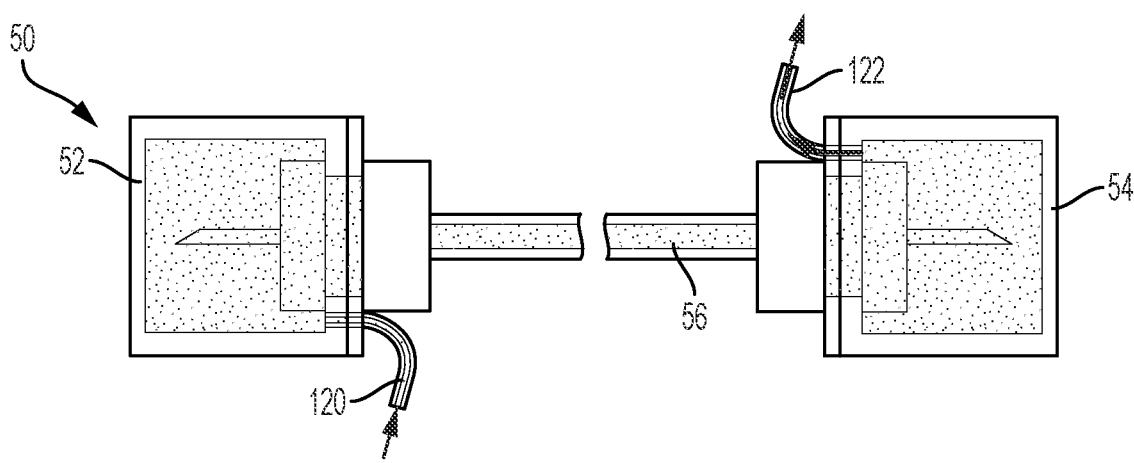
FIG. 24B is a front view of the priming system of FIG. 23 according to one aspect of the present invention, showing an open position of the system with the fluid path filled with fluid.
Figure 25:
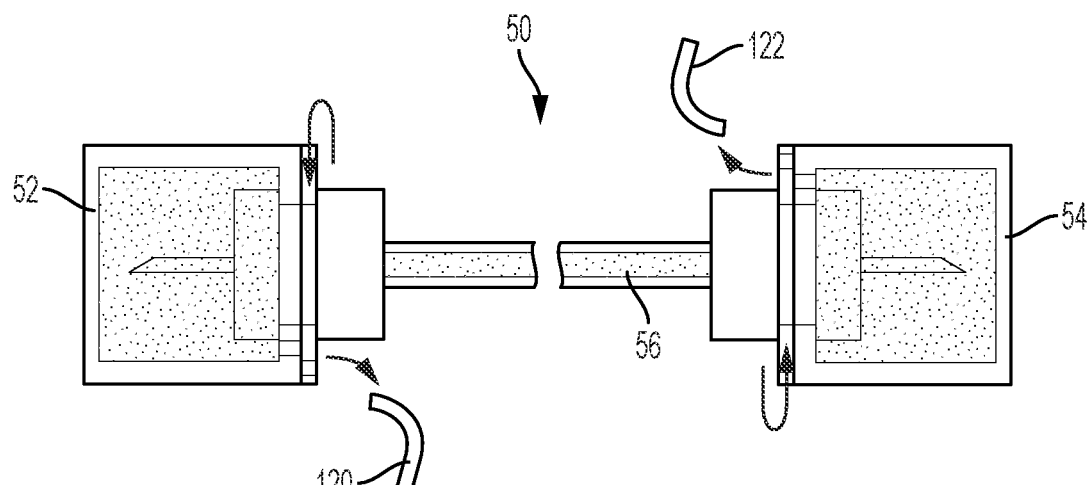
FIG. 25 is a front view of the priming system of FIG. 23 according to one aspect of the present invention, showing a closed position of the system.

Referring to FIGS. 23-25, prior to use of the priming system 50, the priming assemblies 52, 54 and the delivery tube 56 are filled with air and are ready for filling. The priming system 50 is primed by delivering priming fluid through the inflow tube 120 of the cartridge priming assembly 52 with the base 62 in the first position such that fluid flows through the inflow tube 120, through the passageway 64 of the base 62, through the passageway 70 of the cap 66, and into the interior chamber 68 of the cap 66. From the interior chamber 68 of the cap 66, the fluid continues to flow through the needle 72, through the hub, and into the delivery tube 56. With the base 82 of the needle actuator priming assembly 54 in the first position, the fluid flows through the hub 80 of the needle actuator priming assembly 54, through the needle 92, into the interior chamber 88 of the cap 86 of the needle actuator priming assembly 54, and into the outflow tube 122 of the needle actuator priming assembly 54. Once the priming system 50 is fully primed and all air is removed from the system 50, the bases 62, 82 of the cartridge priming assembly 52 and the needle actuator priming assembly 54 are each rotated from the first position to the second position to seal the primed fluid with the priming system 50. When the bases 62, 82 are in the second position, the passageways 64, 84 of the bases 62, 82 are isolated from and are sealed from the passageways 70, 90 of the cap. The priming fluid may be buffered saline, heparin, or any other suitable priming fluid.

Figure 26:
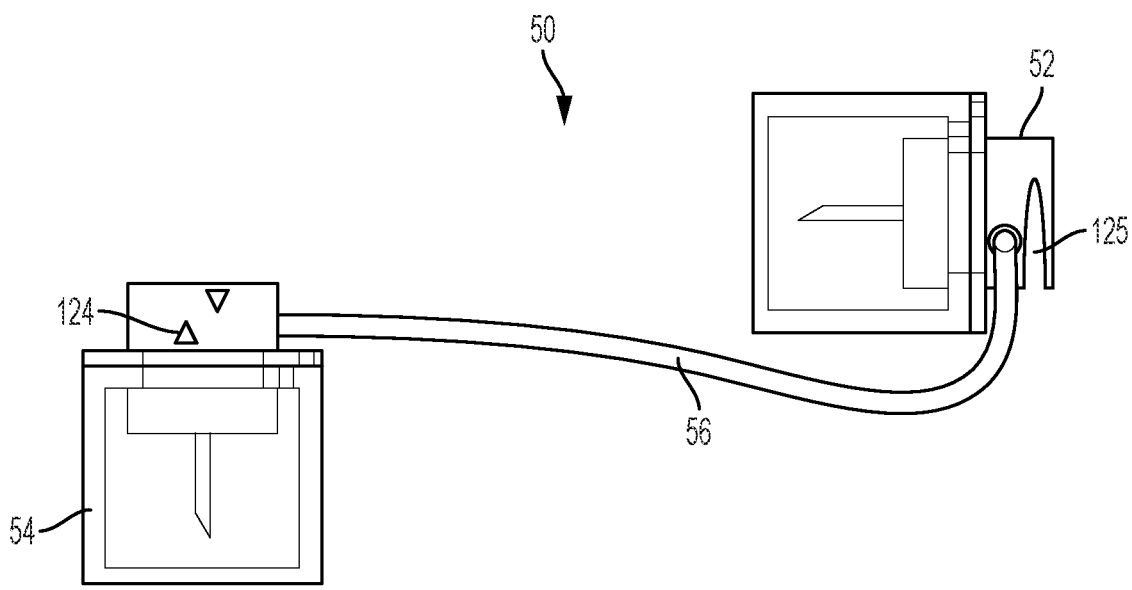
FIG. 26 is a front view of the priming system of FIG. 23 according to one aspect of the present invention, showing drug delivery device interfaces.
Figure 27:
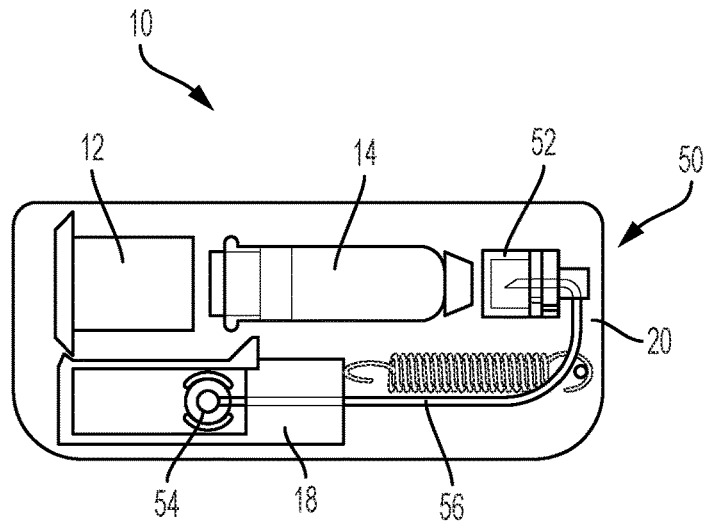
FIG. 27 is a top view of a drug delivery device according to one aspect of the present invention, showing a pre-use position of the device.
Figure 28:
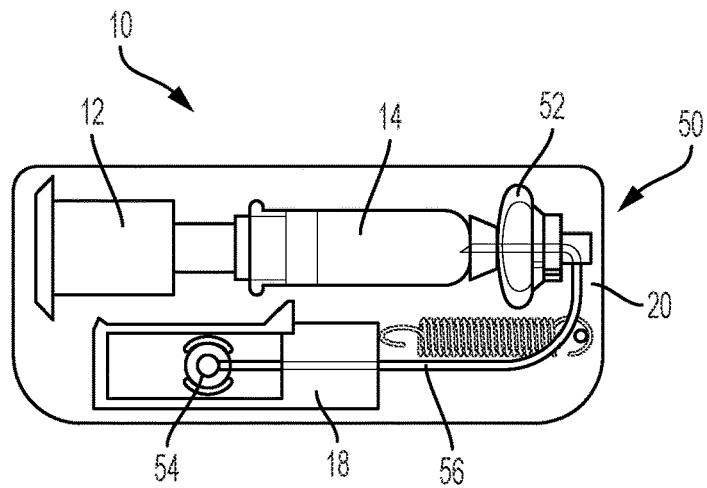
FIG. 28 is a top view of the drug delivery device of FIG. 27 according to one aspect of the present invention, showing a use position of the device.
Figure 29:
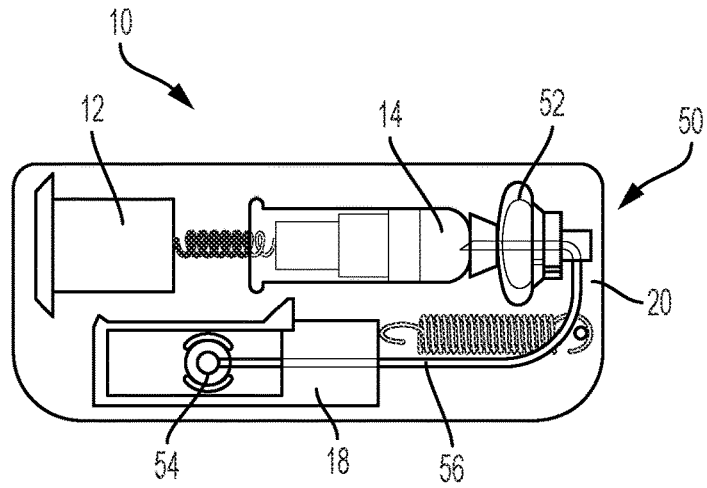
FIG. 29 is a top view of the drug delivery device of FIG. 27 according to one aspect of the present invention, showing a further use position of the device.
Figure 30:
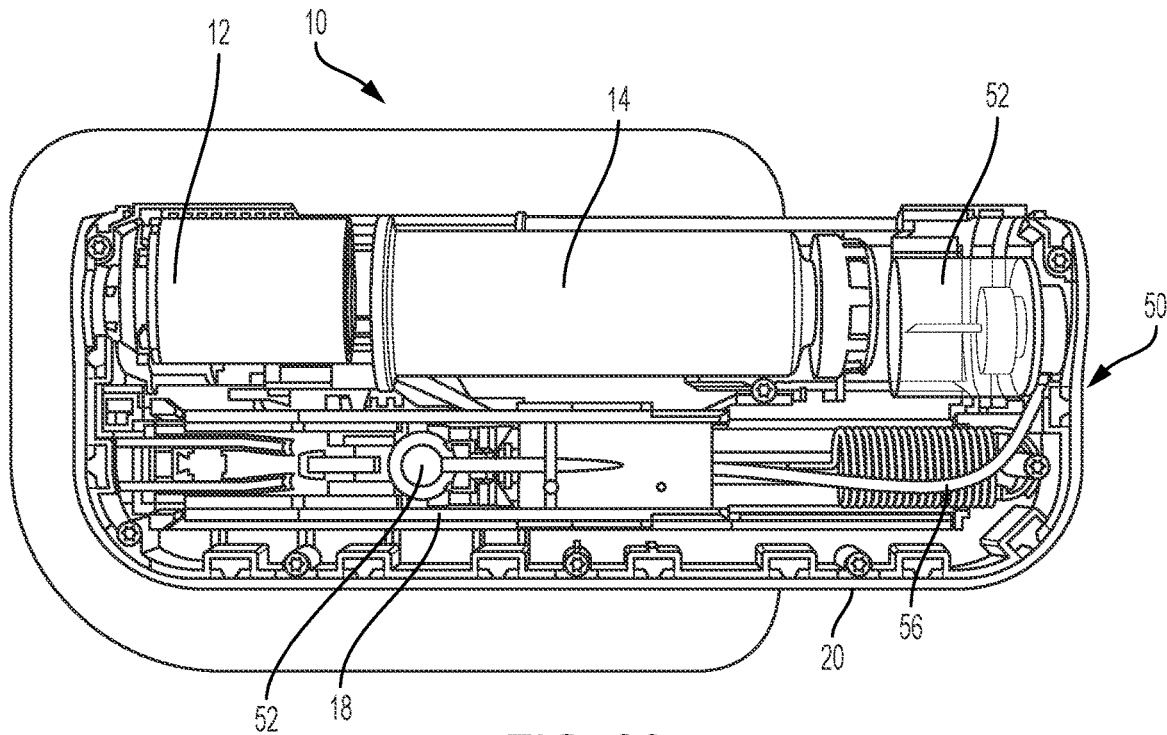
FIG. 30 is a top view of a drug delivery device according to one aspect of the present invention, showing a pre-use position of the device
Figure 31:
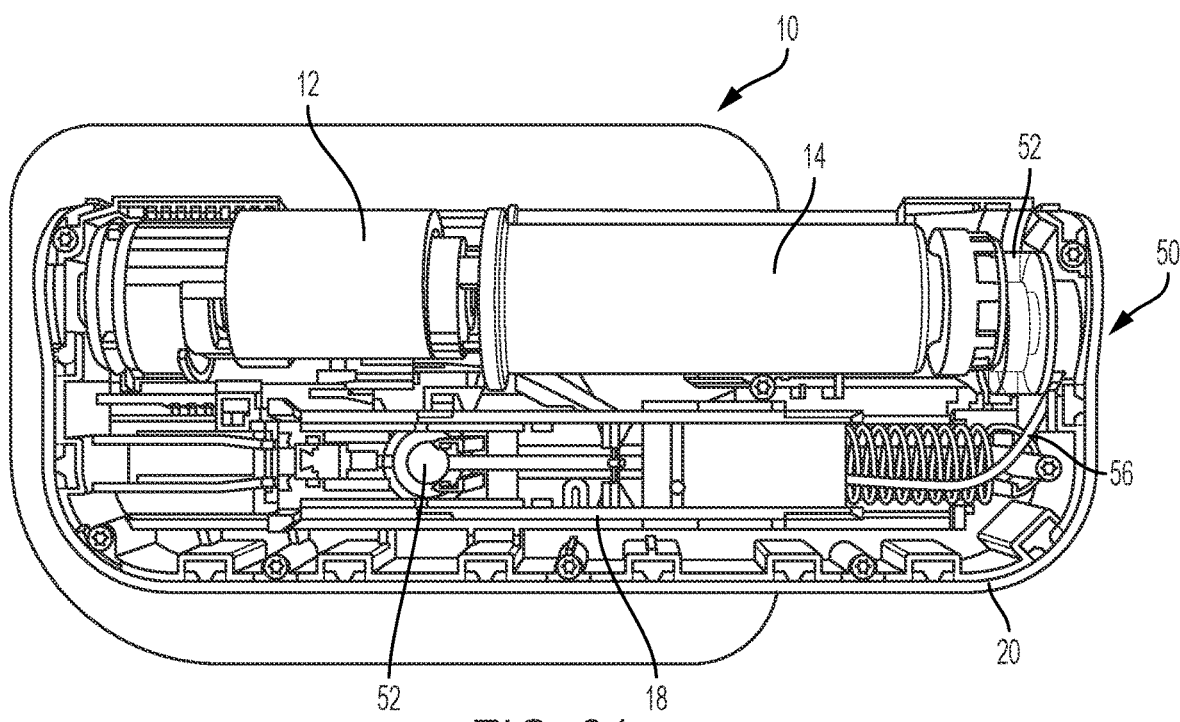
FIG. 31 is a top view of a drug delivery device according to one aspect of the present invention, showing a use position of the device.

Referring to FIGS. 26-31, the priming system 50 is configured to be primed and assembled into the drug delivery device 10. In one aspect, the cartridge priming assembly 52 replaces the valve assembly 16 and the needle actuator priming assembly 54 replaces the needle 28 while functioning the same as the valve assembly 16 and needle 28. As shown in FIG. 26, the cartridge priming assembly 52 and the needle actuator priming assembly 54 include interfaces 124, 125 for cooperating with the device 10 in the same manner as the valve assembly 16 and needle 28. As shown in FIG. 27, in a pre-use state, the priming system 50 is primed and filled with priming fluid. As shown in FIG. 28, during an injection, the cartridge 14 engages the cap 66 of the cartridge priming assembly 52 and deforms the cap 66 to the second position with the needle 72 being placed in fluid communication with the medicament in the cartridge 14. The priming fluid is pushed out by the medicament from the cartridge 14, which flows from the cartridge 14 through the cartridge priming system 52, through the delivery tube 56, and through the needle actuator priming assembly 54 and into a patient. As shown in FIG. 29, during injection, all of the priming fluid has been injected and the medicament from the cartridge 14 is being injected.

Figure 32:
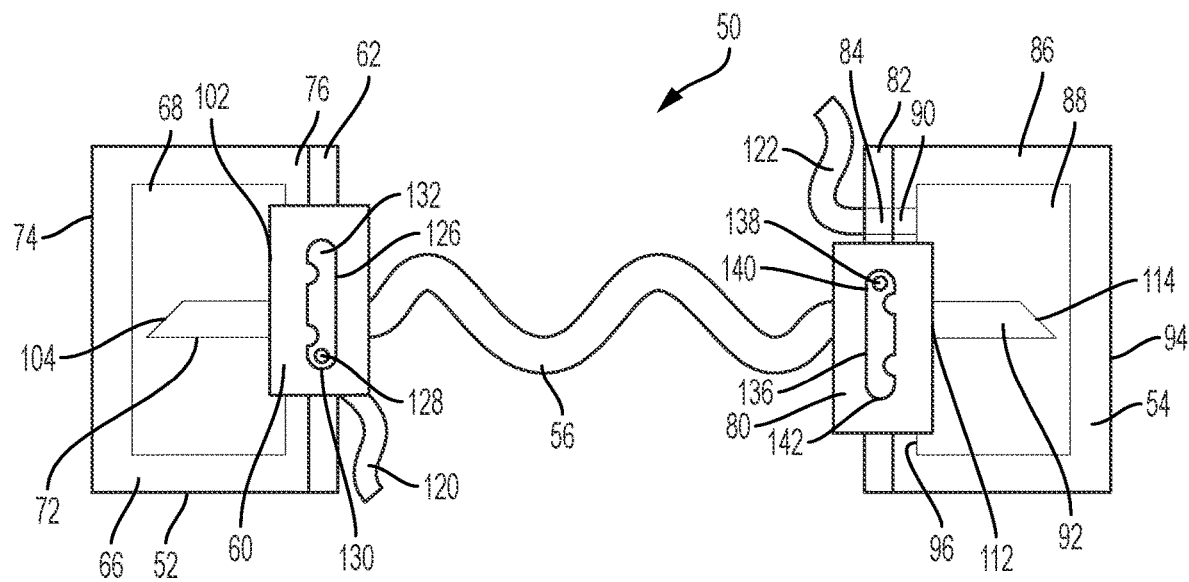
FIG. 32 is a front view of a priming system according to one aspect of the present invention, showing an open position of the system.
Figure 33:
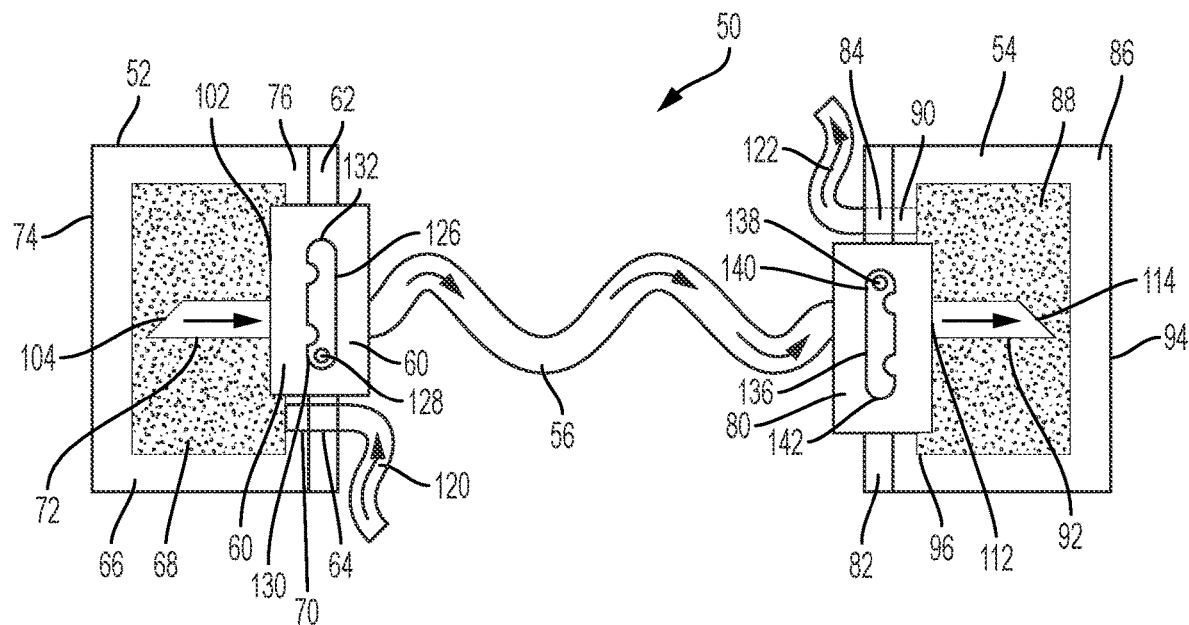
FIG. 33 is a front view of the priming system of FIG. 32 according to one aspect of the present invention, showing an open position of the system while fluid fills the fluid path.
Figure 34:
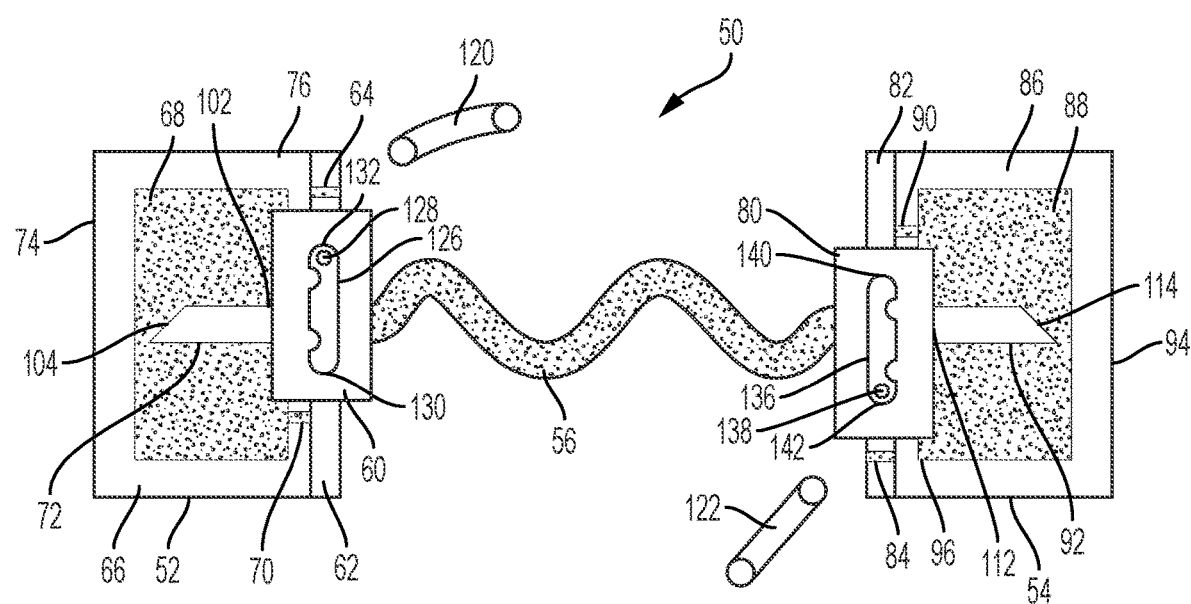
FIG. 34 is a front view of the priming system of FIG. 32 according to one aspect of the present invention, showing a closed position of the system with the fluid path filled with fluid.

Referring to FIGS. 32-34, in one aspect, the hub 60, 80 of the priming assemblies 52, 54 defines a slot 126, 136 and the base 62, 82 includes a projection 128, 138 received within the slot 126, 136. The slot 126, 136 has a first end 130, 140 and a second end 132, 142. When the projection 128, 138 is at the first end 130, 140 of the slot 126, 136, as shown in FIG. 32, the base 62, 82 is in the first position and, when the projection 128, 138 is at the second end of the slot 126, 136, as shown in FIG. 33, the base 62, 82 is in the second position. Accordingly, the base 62, 82 is rotatable between the first and second positions and movement of the base 62, 82 may be restricted to movement between the first and second positions. The slots 126, 136 may include bumps or other structures to retain the projections 128, 138 in the first and second ends 130, 132, 140, 142 of the slots 126, 136. Further, the slot 126, 136 and projection 128, 138 may provide a visual and/or tactile feedback regarding whether the base 62, 82 is in the first position or the second position. Although the slot 126, 136 is provided on the hub 60, 80 and the projection 128, 138 is provided on the base 62, 82, the position of the slot 126, 136 and the projection 128, 138 may be reversed with the base 62, 82 defining the slot 126, 136 and the hub 60, 80 including the projection 128, 138. As shown in FIG. 34, the inflow and outflow tubes 120, 122 may be removed after the priming system 50 is primed and sealed.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A priming assembly for a drug delivery device, the priming assembly comprising:
a hub;
a base connected to the hub and rotatable relative to the hub between a first position and a second position, the base defining a passageway;
a cap defining an interior chamber and a passageway in fluid communication with the interior chamber; and
a needle connected to the hub and positioned within the interior chamber of the cap, wherein the passageway of the base is in fluid communication with the passageway of the cap when the base is in the first position, and wherein the passageway of the base is isolated from the passageway of the cap when the base is in the second position; wherein rotation of the base relative to the hub is restricted to movement between the first position and the second position.

2. The assembly of claim 1, wherein the cap and the base form a sealed interface between the cap and the base.

3. The assembly of claim 1, wherein the cap includes a closed first end and an open second end, the open second end secured to the hub.

4. The assembly of claim 3, wherein the cap comprises an elastomeric material.

5. The assembly of claim 3, wherein the cap is configured to deform from a first position where an end of the needle is positioned within the cap to a second position where the end of the needle is positioned outside of the cap.

6. The assembly of claim 1, wherein one of the hub and the base defines a slot and the other of the hub and the base comprises a projection received within the slot, the slot having a first end and a second end, and wherein, when the projection is at the first end of the slot, the base is in the first position, and, when the projection is at the second end of the slot, the base is in the second position.

7. The assembly of claim 6, wherein the slot includes a first bump to retain the projection in the first end and a second bump to retain the projection in the second end.

8. The assembly of claim 6, wherein the slot and the projection are configured to provide visual and/or tactile feedback whether the base is in the first position or the second position.

9. The assembly of claim 1, further comprising a priming fluid tube in fluid communication with the passageway of the base.

10. The assembly of claim 9, further comprising a delivery tube connected to the hub and in fluid communication with the needle.

11. The assembly of claim 1, wherein the base defines a base passageway.

12. A drug delivery device comprising:
a housing;
a cartridge received within the housing, the cartridge configured to receive a medicament;
a drive assembly received within the housing and configured to engage the cartridge and dispense medicament from the cartridge;
a needle actuator assembly received within the housing, the needle actuator assembly comprising a patient needle configured to pierce a user's skin; and
a priming system comprising:
a cartridge priming assembly comprising a first hub, a first base connected to the first hub and moveable relative to the first hub between a first position and a second position, wherein one of the first hub and the first base defines a first slot and the other of the first hub and the first base comprises a first projection received within the first slot, the first slot having a first end and a second end, and wherein, when the first projection is at the first end of the first slot, the first base is in the first position, and, when the first projection is at the second end of the first slot, the first base is in the second position; and
a needle actuator priming assembly comprising a second hub, a second base connected to the second hub and moveable relative to the second hub between a first position and a second position, wherein one of the second hub and the second base defines a second slot and the other of the second hub and the second base comprises a second projection received within the second slot, the second slot having a first end and a second end, and wherein, when the second projection is at the first end of the second slot, the second base is in the first position, and, when the second projection is at the second end of the second slot, the second base is in the second position.

13. The drug delivery device of claim 12, wherein the cartridge priming assembly further comprises a first cap defining a first interior chamber and a first cap passageway in fluid communication with the first interior chamber, and a first needle connected to the first hub and positioned within the first interior chamber of the first cap, the first base defining a first base passageway, and
wherein the needle actuator priming assembly further comprises a second cap defining a second interior chamber and a second cap passageway in fluid communication with the second interior chamber, and a second needle connected to the second hub and positioned within the second interior chamber of the second cap, the second base defining a second base passageway.

14. The drug delivery device of claim 13, wherein the first base passageway of the cartridge priming assembly is in fluid communication with the first cap passageway of the cartridge priming assembly when the first base is in the first position, and wherein the first base passageway of the cartridge priming assembly is isolated from the first cap passageway when the first base is in the second position.

15. The drug delivery device of claim 13, wherein the second base passageway of the needle actuator priming assembly is in fluid communication with the second cap passageway of the needle actuator priming assembly when the second base is in the first position, and wherein the second base passageway of the needle actuator priming assembly is isolated from the second cap passageway when the second base is in the second position.

16. The drug delivery device of claim 13, further comprising an inflow tube in fluid communication with the first base passageway of the cartridge priming assembly.

17. The drug delivery device of claim 13, further comprising an outflow tube in fluid communication with the second base passageway of the needle actuator priming assembly.

18. The drug delivery device of claim 13, wherein the first cap and the first base of the cartridge priming assembly form a sealed interface between the first cap and the first base, and the second cap and the second base of the needle actuator priming assembly form a sealed interface between the second cap and the second base.

19. The drug delivery device of claim 12, further comprising a delivery tube in fluid communication with the first hub of the cartridge priming assembly and the second hub of the needle actuator priming assembly.

\* \* \* \* \*